(12) United States Patent
Li et al.

(10) Patent No.: US 7,235,654 B2
(45) Date of Patent: Jun. 26, 2007

(54) METHODS FOR MODULATING IKKα ACTIVITY

(75) Inventors: Jun Li, Danbury, CT (US); Xiang Li, Danbury, CT (US); Jianfei Yang, Sandy Hook, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 301 days.

(21) Appl. No.: 10/730,614

(22) Filed: Dec. 8, 2003

(65) Prior Publication Data

US 2005/0043257 A1 Feb. 24, 2005

Related U.S. Application Data

(60) Provisional application No. 60/431,825, filed on Dec. 9, 2002.

(51) Int. Cl.
*C07H 21/02* (2006.01)
*C07H 21/04* (2006.01)

(52) U.S. Cl. .................. 536/24.5; 536/23.1; 536/24.3; 536/24.33

(58) Field of Classification Search ............... 536/23.1, 536/24.3, 24.33, 24.5
See application file for complete search history.

(56) References Cited

U.S. PATENT DOCUMENTS 4,745,119 A 5/1988 Krenitsky

| | | |
|---|---|---|
| 6,235,513 B1 | 5/2001 | Rothe et al. |
| 6,258,579 B1 | 7/2001 | Mercurio et al. |
| 6,395,545 B1 | 5/2002 | Monia et al. |
| 6,649,637 B2 | 11/2003 | Curiel |
| 2002/0132788 A1 | 9/2002 | Lewis et al. |
| 2003/0124726 A1 | 7/2003 | De Fougerolles et al. |
| 2003/0143540 A1 | 7/2003 | Matsuda et al. |
| 2003/0170719 A1 | 9/2003 | Matsuda et al. |
| 2004/0014111 A1* | 1/2004 | Li et al. .................. 435/6 |
| 2006/0073120 A1* | 4/2006 | Li et al. .................. 424/93.2 |

OTHER PUBLICATIONS

A. O'Mahony, et al. "Activation of the Heterodimeric IkB Kinase alpha (IKKalpha)-IKKbeta Complex is Directional: IKKalpha Regulates IKKbeta under both Basal and Stimulated Conditions", Mol. and Cell.Bio., vol. 20, No. 4, pp. 1170-1178, 2000.
I. S. Bhullar, et al. "Fluid Shear Stress Activation of IkB Kinase is Integrin-dependent", J. Bio. Chem. vol. 273, No. 46, pp. 30544-30549, 1998.
M. C.-T. Hu, et al. "IkB kinase-alpha and -beta genes are coexpressed in adult and embryonic tissues but localized to different human chromosomes", Gene, vol. 222, pp. 31-40, 1998.

(Continued)

*Primary Examiner*—Sean McGarry
*Assistant Examiner*—Terra C. Gibbs
(74) *Attorney, Agent, or Firm*—Michael Morris; Mary-Ellen M. Devlin; David Dow

(57) ABSTRACT

A method for modulating NF-κB dependent gene transcription in a cell comprised of modulating IKKα protein activity in the cell. The present invention also provides siRNA compositions and methods thereof for modulating NF-κB dependent gene transcription.

3 Claims, 3 Drawing Sheets

Data from Affymetrix human U133 arrays show that IKKα_3 siRNA (compared to the IKKα_3_inverted control siRNA oligos) specifically inhibited the mRNA expression of IKKα but had no effect on IKKβ
5  mRNA expression.

OTHER PUBLICATIONS

J. D. Thompson "Applications of antisense and siRNAs during preclinical drug development", Drug Discovery Today, vol. 7, No. 17, pp. 912-917, 2002.

S. Agrawal, et al. "Antisense therapeutics: is it as simple as complementary base recognition?", Mol. Med. Today, vol. 6, pp. 72-81, 2000.

Pahl, H.L., "Activators and Target Genes of Rel/NF-kB Transription Factors", Oncogene, 1999, vol. 18, pp. 6853-6866.

Mercurio, F., et al. "NF-kB as a Primary Regulator of the Stress Response", Oncogene, 1999, vol. 18, pp. 6163-6171.

Barkett, M., et al. "Control of Apoptosis by Rel/NF-kB Transcription Factors", Oncogene, 1999, vol. 18, pp. 6910-6924.

Karin, M., "How NF-kB is activated: The Role of the IkB Kinase (IKK) Complex", Oncogene, 1999, vol. 18, pp. 6867-6874.

Jiang, M., et al. "Selective Silencing of Viral Gene Expression in HPV-Positive Human Cervical Carcinoma Cells Treated with siRNA, a Primer of RNA Interference", Oncogene, 2002, vol. 21, pp. 6041-6048.

Jobin, C., et al. "The IkB/NF-kB System: A Key Determinant of Mucosal Inflammation and Protection", American Journal of Physiology, Cellular Physiology, vol. 278, pp. 451-462, 2000.

Siebenlist, U., et al.; "Structure, Regulation and Function of NF-kappaB"; Annual Review of Cell Biology, Nov. 1994, vol. 10, pp. 405-455.

Baldwin, A., Jr., et al. "The NF-kB and IkB Proteins: New Discoveries and Insights", Annual Review of Immunology, 1996, vol. 14, pp. 649-681.

Ghosh, S., et al., "NF-kB and Rel Proteins: Evolutionarily Conserved Mediators of Immune Responses", Annual Review of Immunology, 1998, vol. 16, pp. 225-260.

Li, Z. W., et al. "The IKKb Subunit of IkB Kinase (IKK) is Essential for Nuclear Factor kB Activation and Prevention of Apoptosis", Journal of Experimental Medicine, 1999, vol. 189, No. 11, pp. 1839-1845.

Li, X., et al. "IKKa, IKKb, and NEMO/IKKy Are Each Required for the NF-kB-Mediated Inflammatory Response Program", The Journal of Biological Chemistry, 2002, vol. 277, No. 47, pp. 45129-45140.

Hu, Y., et al, "Abnormal Morphogenesis But Intact IKK Activation in Mice Lacking the IKKa Subunit of IkB Kinase", Science, 1999, vol. 284, pp. 316-320.

Anest, V., et al. "A Nucleosomal Function for IkB Kinase-a In NF-kB-dependent Gene Expression", Nature, 2003, vol. 423, pp. 659-663.

Fire, A., et al., "Potent and Specific Genetic Interference by Double-Stranded RNA in Caenorhabditis Elegans", Nature, 1998, vol. 391, pp. 806-811.

Elbashir, S. M., et al. "Duplexes of 21-nucleotide RNAs Mediate RNA Interference in Cultured Mammalian Cells", Nature, 2001, vol. 411, pp. 494-498.

Hannon, G.J., et al. "RNA Interference", Nature, 2002, vol. 418, pp. 244-250.

Sharp, P.A., et al. "sIRNA-directed inhibition of HIV-1 Infection", Nature Medicine, 2002, vol. 8, pp. 681-687.

Irie, N., et al. "Subtype-and Species-Specific Knockdown of PKC using Short Interfering RNA", Biochemical and Biophysical Research Communications, 2002, vol. 298, pp. 738-743.

Sharp, P.A., "RNA Interference - 2001", Genes and Development, 2001, vol. 15, pp. 485-490.

McManus, M.T., et al. "Small Interfering RNA-Mediated Gene Silencing in T Lymphocytes", Journal of Immunology, 2002, vol. 169, pp. 5754-5760.

Charles A. Parkos, et al. "Primary structure and unique expression of the 22-kilodaiton light chain of human neutrophll cytochrome beta"; Proc. Natl. Acad. Sci. USA; vol. 85, pp. 3319-3323; 1988.

Fang Qian, et al. "The Structure of the Mouse Cathepsin B Gene and Its Putative Promoter"; DNA and Cell Biology, vol. 10, No. 3, pp. 159-168, 1991.

Mark E. Rosenberg, et al. "Clusterin: Physiologic and Pathophysiologic Considerations"; Int. J. Biochem. Cell. Biol., vol. 27, No. 7, pp. 633-645, 1995.

Yinling Hu, et al. "IKKalpha controls formation of the epidermis independently of NF-kB"; NATURE , vol. 410, pp. 710-714, 2001.

Amer A. Beg, et al. "Embryonic Lethality and Liver Degeneration in Mice Lacking the RelA Component of NF-kB"; NATURE; vol. 376; pp. 167-170, 1995.

Robyn Starr, et al. "A Family of Cytokine-Inducible Inhibitors of Signalling"; NATURE, vol. 387, pp. 917-921, 1997.

Mary C. Dinauer, et al. "Human Neutrophil Cytochrome b Light Chain (p22-phox)" J. Clin. Invest. vol. 86, pp. 1729-1737, 1990.

John R. Silkensen, et al. "The Role of Clusterin in Tissue Injury", Biochem. Cell. Biol. vol. 72, pp. 483-488, 1994.

Constantin Makris, et al. "Femal Mice Heterozygous for IKKy/NEMO Deficiencies Develop a Dermatopathy Similar to the Human X-Linked Disorder Incontinentia Pigmentl"; Molecular Cell, vol. 5, pp. 969-979, 2000.

Marc Schmidt-Supprian, et al. "NEMO/IKKy-Deficient Mice Model Incontinentia Pigmentl" Molecular Cell, vol. 5, pp. 981-992, 2000.

Yixue Cao, et al. "IKKalpha Provides an Essential Link between RANK Signaling and Cyclin D1 Expression during Mammary Gland Development", Cell, vol. 107, pp. 763-775, 2001.

Vigo Heissmeyer, et al. "Shared Pathways of IkB Kinase-Induced SCF -Mediated Ubiquitination and Degradation for the NF-kB Precursor p105 and IbBalpha", Mol. Cell. Biol. vol. 21, No. 4, pp. 1024-1035, 2001.

Mark E. Rosenberg, et al. "Apollpoprotein J/Clusterin Prevents a Progressive Glomerulopathy of Aging", Mol. Cell. Biol., vol. 22, No. 6, pp. 1893-1902, 2002.

Tommaso Zanocco-Marani, et al. "Biological Activities and Signaling Pathways of the Granulin/Epithelin Precursor", Cancer Research, vol. 59, pp. 5331-5340, 1999.

Minoru Tanaka, et al. "Reconstitution of the Functional Mouse Oncostatin M (OSM) Receptor: Molecular Cloning of the Mouse OSM Receptor Beta Subunit", Blood, vol. 93, No. 3, pp. 804-815, 1999.

John C. Groskopf, et al. "Proliferin Induces Endothelial Cell Chemotaxis through a G Protein-Coupled, Mitogen-Activated Protein Kinase-Dependent Pathway", Endocrinology, vol. 138, No. 7, pp. 2835-2840, 1997.

Daniel J. Toft, et al. "Reactivation of Proliferin gene expression is associated with increased anglogenesis in a cell culture model of fibrosarcoma tumor progression", PNAS, vol. 98, No. 23, pp. 13055-13059, 2001.

Steven S. Smith, et al. "Mechanism of Human Methyl-directed DNA methyltransferase and the fidelity of cytosine methylation", Proc. Natl. Acad. Sci. USA, vol. 89, pp. 4744-4748, 1992.

Yujing Liu, et al. "Mouse model of G activator deficiency manifests cerebellar pathology and motor impairment", Proc. Natl. Acad. Sci. USA, vol. 94, pp. 8138-8143, 1997.

Chiara Berlato, et al. "Involvement of Suppressor of Cytokine Signaling-3 as a Mediator of the Inhibitory Effects of IL-10 on Lipopolysaccharide-Induced Macrophage Activation", The Journal of Immunology, vol. 168, 6404-6411, 2002.

Norio Matsushima, et al. "Super-Motifs and Evolution of Tandem Leucine-Rich Repeats Within the Small Proteoglycans--Biglycan, Decorin, Lumican, Fibromodulin, PRELP, Keratocan, Osteoadherin, Epiphycan, and Osteoglycin" PROTEINS vol. 38; pp. 210-225 2000.

Leo W.J. Klomp, et al. "Ceruloplasmin Gene Expression in the Murine Central Nervous System" J. Clin. Invest. vol. 98, No. 1, pp. 207-215 1996.

Nobuaki Shimizu, et al. "A Putative G Protein-Coupled Receptor, RDC1, Is a Novel Coreceptor for Human and Simian Immunodeficiency Viruses"; J. of Virology, vol. 74, No. 2, pp. 619-626, 2000.

Rosemarie Panetta, et al. "Regulators of G-Protein Signaling (RGS) 1 and 16 are Induced in Response to Bacterial Lipopolysaccharide and Stimulate c-fos Promoter Expression", Biochem. and Biophys. Research Comm., vol. 259, pp. 550-556, 1999.

Carol Beadling, et al. "Regulators of G Protein Signaling Exhibit Distinct Patterns of Gene Expression and Target G Protein Specificity in Human Lymphocytes", J. Immunology, vol. 162, pp. 2677-2682, 1999.

Ulrich Boehm, et al. "Two Families of GTPases Dominate the Complex Cellular Response to IFN-y1" J. Immunology, vol. 161, pp. 6715-6723, 1998.

Thomas A. Wynn, et al. "Indentification and Characterization of a New Gene Family Iduced During Macrophage Activation", J. Immunology, vol. 147, No. 12, pp. 4384-4392, 1991.

Dorothea Rudolph, et al. "Severe liver degeneration and lack of NF-kB activation in NEMO/IKKy-deficient mice" Genes and Development, vol. 14, pp. 854-862, 2000.

Smith, et al., Oral Use of Interferon-Alpha Stimulates ISG-15 Transcription and Production by Human Buccal Epithelial Cells, Journal of Interferon and Cytokine Research, 1999, vol. 19, pp. 923-928.

Seymour Katz, "Update in Medical Therapy of Ulcerative Colitis", Journal of Clinical Gastroenterology, 2002, vol. 34, pp. 397-407.

Jun Li, et al. "Recombinant lkB Kinases alpha and beta Are Direct Kinases of lkBalpha"; J. Biol. Chem., vol. 273, No. 46, pp. 30736-30741, 1998.

Michael J. May, et al. "Selective Inhibition of NF-kB Activation by a Peptide That Blocks the Interaction of NEMO with the lkB Kinase Complex"; SCIENCE, vol. 289, pp. 1550-1554, 2000.

Qiutang Li, et al. "Severe Liver Degeneration in Mice Lacking the IkB Kinase 2 Gene"; SCIENCE, vol. 284, pp. 321-325, 1999.

Mireille Delhase, et al. "Positive and Negative Regulation of lkB Kinase Activity Through IKKB Subunit Phosphorylation"; SCIENCE, vol. 284, pp. 309-313, 1999.

Uwe Senftleben, et al. "Activation by IKKalpha of a Second, Evolutionary Conserved, NF-kB Signaling Pathway"; SCIENCE, vol. 293, pp. 1495-1499, 2001.

Yumi Yamamoto, et al. "IKKy/NEMO Facilitates the Recruitment of the IkB Proteins into the lkB Kinase Complex"; J. Biol. Chem., vol. 276, No. 39, pp. 36327-36336, 2001.

Jun Li, et al. "Novel NEMO/lkB Kinase and NF-kB Target Genes at the Pre-B to Immature B Cell Transition"; J. Biol. Chem., vol. 276, No. 21, pp. 18579-18590, 2001.

Nywana Sizemore, et al. "Distinct Roles of the lkB Kinase alpha and beta Subunits in Liberating Nuclear Factor kB (NF-kB) from lkB and in Phosphorylating the p65 Subunit of NF-kB"; J. Biol. Chem. vol. 277, No. 6, pp. 3863-3869, 2000.

Yuji Shirakata, et al. "Epiregulin, a Novel Member of the Epidermal Growth Factor Family, is an Autocrine Growth Factor in Normal Human Keratinocytes"; J. Biol. Chem. vol. 275, No. 8, pp. 5748-5753, 2000.

Beverly Rothermel, et al. "A Protein Encoded within the Down Syndrome Critical Region is Enriched in Striated Muscles and Inhibits Calcineurin Signaling"; J. Biol. Chem., vol. 275, No. 12, pp. 8719-8725, 2000.

Angela R. Aldred, et al. "Rat Ceruloplasmin: Molecular Cloning and Gene Expression In Liver, Choroid Plexus, Yolk Sac, Placenta, and Testis", J. Biol. Chem. vol. 262, No. 6, pp. 2875-2878, 1987.

Erik G. Lund, et al. "cDNA Cloning of Mouse and Human Cholesterol 25-Hydroxylases, Polytopic Membrane Proteins that Synthesize a Potent Oxysterol Regulator of Lipid Metabolism", J. Biol. Chem. vol. 273, No. 51, pp. 34316-34327, 1998.

Inigo Santamaria, et al. "Cathepsin Z, a Novel Human Cysteine Proteinase with a Short Propeptide Domain and a Unique Chromosomal Location", J. Biol. Chem. vol. 273, No. 27, pp. 16816-16823, 1998.

Inigo Santamaria, et al. "Molecular Cloning and Structural and Functional Characterization of Human Cathepsin F, a New Cysteine Proteinase of the Papain Family with a Long Propeptide Domain", J. Biol. Chem. vol. 274, No. 20, pp. 13800-13809, 1999.

Tsuneyasu Kaisho, et al. "lkB Kinase alpha Is Essential for Mature B Cell Development and Function", J. Exp. Med. vol. 193, No. 4, pp. 417-426, 2001.

Michael Karin, et al. "Phosphorylation Meets Ublquitination: The Control of NF-kB Activity", Ann. Rev. Immunology. vol. 18, pp. 621-663, 2000.

Akemi Matsushima, et al. "Essential Role of Nuclear Factor (NF)-kB-inducing Kinase and Inhibitor of kB (lkB) Kinase alpha in NF-kB Activation through Lymphotoxin Beta Receptor, but Not through Tumor Necrosis Factor Receptor I", J. Exp. Med. vol. 193, No. 5, pp. 631-636, 2001.

Inder M. Verma, et al. "Rel/NF-kB/lkB Family: Intimate tales of association and dissociation", Genes & Development, vol. 9, pp. 2723-2735, 1995.

Conrad C. Bleul, et al. "A Highly Efficacious Lymphocyte Chemoattractant, Stromal Cell-derived Factor 1 (SDF-1)", J. Exp. Med., vol. 184, pp. 1101-1109, 1996.

Vigo Heissmeyer, et al. "NF-kB p105 is a target of lkB kinases and controls signal induction of Bcl-3-p50 complexes", The EMBO Journal, vol. 18, No. 17, pp. 4766-4778, 1999.

Giichi Takaesu, et al. "TAK1 is Critical for lkB Kinase-mediated Activation of the NF-kB Pathway", J. Mol. Biol., vol. 326, pp. 105-115, 2003.

Wathelet, et al. "2-Aminopurine selectively blocks the transcriptional activation of cellular genes by virus, double-stranded RNA and Interferons in Human cells", European Journal of Biochemistry, 1989, vol. 184, pp. 503-509.

Manthey, et al. "SB202190, a selective inhibitor of p38 mitogen-activated protein kinase, is a poweful regulator of LPS-induced mRNAs inmonocytes", Journal of Leukocyte Biology, 1998, vol. 64, pp. 409-417.

* cited by examiner

Data from Affymetrix human U133 arrays show that IKKα_3 siRNA (compared to the IKKα_3_inverted control siRNA oligos) specifically inhibited the mRNA expression of IKKα but had no effect on IKKβ mRNA expression.

SiRNA of IKKα inhibits IKKα, IL-6 and IL-8 expression in HeLa cells. HeLa cells were transfected with IKKα_3 siRNA or IKKa_3ivt (sequence inverted control oligos of IKKα_3, then induced with or without TNFα. IKKα, IL-6 and IL-8 mRNA copy numbers were determined by TaqMan.

IKKα_3 siRNA inhbited TNFα-induced NF-kB activity in HeLa cells. HeLa cells (stably transfected with NF-κB-Luciferase reporter) were transfected with siRNAs for 2 days. Cells were then stimulated with TNFα (10 ng/ml) for 24 hr and the luciferase activity was measured. IKKα_3 siRNA inhibited NF-κB-depenent luciferase activity in respond to TNFα.

SEQUENCE LISTING

<160> NUMBER OF SEQ ID NOS: 11

<210> SEQ ID NO 1
<211> LENGTH: 2238
<212> TYPE: DNA
<213> ORGANISM: Homo sapiens

<400> SEQUENCE: 1

```
atggagcggc ccccggggct gcggccgggc gcgggcgggc cctgggagat gcgggagcgg      60
ctgggcaccg gcggcttcgg gaacgtctgt ctgtaccagc atcgggaact tgatctcaaa     120
atagcaatta agtcttgtcg cctagagcta agtaccaaaa acagagaacg atggtgccat     180
gaaatccaga ttatgaagaa gttgaaccat gccaatgttg taaaggcctg tgatgttcct     240
gaagaattga atattttgat tcatgatgtg cctcttctag caatggaata ctgttctgga     300
ggagatctcc gaaagctgct caacaaacca gaaaattgtt gtggacttaa agaaagccag     360
atactttctt tactaagtga tatagggtct gggattcgat atttgcatga aaacaaaatt     420
atacatcgag atctaaaacc tgaaaacata gttcttcagg atgttggtgg aaagataata     480
cataaaataa ttgatctggg atatgccaaa gatgttgatc aaggaagtct gtgtacatct     540
tttgtgggaa cactgcagta tctggcccca gagctctttg agaataagcc ttacacagcc     600
actgttgatt attggagctt tgggaccatg gtatttgaat gtattgctgg atataggcct     660
tttttgcatc atctgcagcc atttacctgg catgagaaga ttaagaagaa ggatccaaag     720
tgtatatttg catgtgaaga gatgtcagga gaagttcggt ttagtagcca tttacctcaa     780
ccaaatagcc tttgtagttt aatagtagaa cccatggaaa actggctaca gttgatgttg     840
aattgggacc ctcagcagag aggaggacct gttgacctta ctttgaagca gccaagatgt     900
tttgtattaa tggatcacat tttgaatttg aagatagtac acatcctaaa tatgacttct     960
gcaaagataa tttcttttct gttaccacct gatgaaagtc ttcattcact acagtctcgt    1020
attgagcgtg aaactggaat aaatactggt tctcaagaac ttctttcaga gacaggaatt    1080
tctctggatc ctcggaaacc agcctctcaa tgtgttctag atggagttag aggctgtgat    1140
agctatatgg tttatttgtt tgataaaagt aaaactgtat atgaagggcc atttgcttcc    1200
agaagtttat ctgattgtgt aaattatatt gtacaggaca gcaaaataca gcttccaatt    1260
atacagctgc gtaaagtgtg ggctgaagca gtgcactatg tgtctggact aaaagaagac    1320
tatagcaggc tctttcaggg acaaagggca gcaatgttaa gtcttcttag atataatgct    1380
aacttaacaa aaatgaagaa cactttgatc tcagcatcac aacaactgaa agctaaattg    1440 gagtttttc acaaaagcat tcagcttgac ttggagagat acagcgagca gatgacgtat    1500
gggatatctt cagaaaaaat gctaaaagca tggaaagaaa tggaagaaaa ggccatccac    1560
```

```
tatgctgagg ttggtgtcat tggatacctg gaggatcaga ttatgtcttt gcatgctgaa    1620
atcatggagc tacagaagag cccctatgga agacgtcagg gagacttgat ggaatctctg    1680
gaacagcgtg ccattgatct atataagcag ttaaaacaca gaccttcaga tcactcctac    1740
agtgacagca cagagatggt gaaaatcatt gtgcacactg tgcagagtca ggaccgtgtg    1800
ctcaaggagc tgtttggtca tttgagcaag ttgttgggct gtaagcagaa gattattgat    1860
ctactcccta aggtggaagt ggccctcagt aatatcaaag aagctgacaa tactgtcatg    1920
ttcatgcagg gaaaaggca gaaagaaata tggcatctcc ttaaaattgc ctgtacacag    1980
agttctgccc ggtcccttgt aggatccagt ctagaaggtg cagtaacccc tcagacatca    2040
gcatggctgc ccccgacttc agcagaacat gatcattctc tgtcatgtgt ggtaactcct    2100
caagatgggg agacttcagc acaaatgata gaagaaaatt tgaactgcct tggccattta    2160
agcactatta ttcatgaggc aaatgaggaa cagggcaata gtatgatgaa tcttgattgg    2220
agttggttaa cagaatga                                                  2238

<210> SEQ ID NO 2
<211> LENGTH: 21
<212> TYPE: DNA
<213> ORGANISM: Homo sapiens
<220> FEATURE:
<221> NAME/KEY: misc_feature
<222> LOCATION: (20)..(21)
<223> OTHER INFORMATION: Any "N" is a (2'-deoxy) thymidine. SI RNA
      Sequence (DNA/RNA)

<400> SEQUENCE: 2
gcagugcacu augugucugn n                                               21

<210> SEQ ID NO 3
<211> LENGTH: 21
<212> TYPE: DNA
<213> ORGANISM: Homo sapiens
<220> FEATURE:
<221> NAME/KEY: misc_feature
<222> LOCATION: (20)..(21)
<223> OTHER INFORMATION: Any "N" is a (2'-deoxy) thymidine. SI RNA
      Sequence (DNA/RNA)

<400> SEQUENCE: 3
gucuguguau cacgugacgn n                                               21

<210> SEQ ID NO 4
<211> LENGTH: 21
<212> TYPE: DNA
<213> ORGANISM: Homo sapiens
<220> FEATURE:
<221> NAME/KEY: misc_feature
<222> LOCATION: (20)..(21)
<223> OTHER INFORMATION: Any "N" is a (2'-deoxy) thymidine. SI RNA
      Sequence (DNA/RNA)

<400> SEQUENCE: 4
cacugcagua ucuggccccn n                                               21

<210> SEQ ID NO 5
<211> LENGTH: 21
<212> TYPE: DNA
<213> ORGANISM: Homo sapiens
<220> FEATURE:
<221> NAME/KEY: misc_feature
<222> LOCATION: (20)..(21)
<223> OTHER INFORMATION: Any "N" is a (2'-deoxy) thymidine. SI RNA
      Sequence (DNA/RNA)
```

```
<400> SEQUENCE: 5
uugggacccu cagcagagan n                                              21

<210> SEQ ID NO 6
<211> LENGTH: 21
<212> TYPE: DNA
<213> ORGANISM: Homo sapiens
<220> FEATURE:
<221> NAME/KEY: misc_feature
<222> LOCATION: (20)..(21)
<223> OTHER INFORMATION: Any "N" is a (2'-deoxy) thymidine. SI RNA
      Sequence (DNA/RNA)

<400> SEQUENCE: 6
ggccauccac uaugcugagn n                                              21

<210> SEQ ID NO 7
<211> LENGTH: 21
<212> TYPE: DNA
<213> ORGANISM: Homo sapiens
<220> FEATURE:
<221> NAME/KEY: misc_feature
<222> LOCATION: (20)..(21)
<223> OTHER INFORMATION: Any "N" is a (2'-deoxy) thymidine. SI RNA
      Sequence (DNA/RNA)

<400> SEQUENCE: 7
gagucguauc accuaccggn n                                              21

<210> SEQ ID NO 8
<211> LENGTH: 745
<212> TYPE: PRT
<213> ORGANISM: Homo sapiens

<400> SEQUENCE: 8
```

Met Glu Arg Pro Pro Gly Leu Arg Pro Gly Ala Gly Gly Pro Trp Glu
1               5                   10                  15

Met Arg Glu Arg Leu Gly Thr Gly Gly Phe Gly Asn Val Cys Leu Tyr
            20                  25                  30

Gln His Arg Glu Leu Asp Leu Lys Ile Ala Ile Lys Ser Cys Arg Leu
        35                  40                  45

Glu Leu Ser Thr Lys Asn Arg Glu Arg Trp Cys His Glu Ile Gln Ile
    50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

```
Phe Glu Asn Lys Pro Tyr Thr Ala Thr Val Asp Tyr Trp Ser Phe Gly
            195                 200                 205

Thr Met Val Phe Glu Cys Ile Ala Gly Tyr Arg Pro Phe Leu His His
        210                 215                 220

Leu Gln Pro Phe Thr Trp His Glu Lys Ile Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
        290                 295                 300

Asp His Ile Leu Asn Leu Lys Ile Val His Ile Leu Asn Met Thr Ser
305                 310                 315                 320

Ala Lys Ile Ile Ser Phe Leu Pro Pro Asp Glu Ser Leu His Ser
                325                 330                 335

Leu Gln Ser Arg Ile Glu Arg Glu Thr Gly Ile Asn Thr Gly Ser Gln
            340                 345                 350

Glu Leu Leu Ser Glu Thr Gly Ile Ser Leu Asp Pro Arg Lys Pro Ala
        355                 360                 365

Ser Gln Cys Val Leu Asp Gly Val Arg Gly Cys Asp Ser Tyr Met Val
370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
        450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Glu Leu
        530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
        595                 600                 605

Ser Lys Leu Leu Gly Cys Lys Gln Lys Ile Ile Asp Leu Leu Pro Lys
```

```
                610             615             620
Val Glu Val Ala Leu Ser Asn Ile Lys Glu Ala Asp Asn Thr Val Met
625                     630                     635             640

Phe Met Gln Gly Lys Arg Gln Lys Glu Ile Trp His Leu Leu Lys Ile
                645                     650                     655

Ala Cys Thr Gln Ser Ser Ala Arg Ser Leu Val Gly Ser Ser Leu Glu
                660                     665                     670

Gly Ala Val Thr Pro Gln Thr Ser Ala Trp Leu Pro Pro Thr Ser Ala
                675                     680                     685

Glu His Asp His Ser Leu Ser Cys Val Val Thr Pro Gln Asp Gly Glu
690                     695                     700

Thr Ser Ala Gln Met Ile Glu Glu Asn Leu Asn Cys Leu Gly His Leu
705                     710                     715                     720

Ser Thr Ile Ile His Glu Ala Asn Glu Glu Gln Gly Asn Ser Met Met
                        725                     730                     735

Asn Leu Asp Trp Ser Trp Leu Thr Glu
                740                     745

<210> SEQ ID NO 9
<211> LENGTH: 24
<212> TYPE: DNA
<213> ORGANISM: Homo sapiens

<400> SEQUENCE: 9
gcacagagat ggtgaaaatc attg                                          24

<210> SEQ ID NO 10
<211> LENGTH: 24
<212> TYPE: DNA
<213> ORGANISM: Homo sapiens

<400> SEQUENCE: 10
caacttgctc aaatgaccaa acag                                          24

<210> SEQ ID NO 11
<211> LENGTH: 24
<212> TYPE: DNA
<213> ORGANISM: Homo sapiens

<400> SEQUENCE: 11
tgagcacacg gtcctgactc tgca                                          24
```

METHODS FOR MODULATING IKKα ACTIVITY

CROSS-REFERENCE TO RELATED APPLICATIONS

This patent application claims benefit to U.S. provisional patent application No. 60/431,825, filed Dec. 9, 2002.

BACKGROUND OF THE INVENTION

This invention relates to the field of, inflammatory diseases and autoimmune diseases and the treatment thereof through the modulation of IKKα activity and the modulation of genes under the control of IKKα.

BACKGROUND INFORMATION

The NF-κB or nuclear factor κB is a transcription factor that plays a critical role in inflammatory diseases by inducing the expression of a large number of proinflammatory and anti-apoptotic genes. These include cytokines such as IL-1, IL-2, IL-11, TNF-α and IL-6, chemokines including IL-8, GRO1 and RANTES, as well as other proinflammatory molecules including COX-2 and cell adhesion molecules such as ICAM-1, VCAM-1, and E-selectin. Pahl H L, (1999) *Oncogene* 18, 6853–6866; Jobin et al, (2000) *Am. J. Physiol. Cell. Physiol.* 278: 451–462. Under resting conditions, NF-κB is present in the cytosol of cells as a complex with IκB. The IκB family of proteins serve as inhibitors of NF-κB, interfering with the function of its nuclear localization signal (see for example U. Siebenlist et al, (1994) *Ann. Rev. Cell Bio.*, 10: 405). Upon disruption of the IκB-NF-κB complex following cell activation, NF-κB translocates to the nucleus and activates gene transcription. Disruption of the IκB-NF-κB complex and subsequent activation of NF-κB is initiated by degradation of IκB.

Activators of NF-κB mediate the site-specific phosphorylation of two amino terminal serines in each IκB which makes nearby lysines targets for ubiquitination, thereby resulting in IκB proteasomal destruction. NF-κB is then free to translocate to the nucleus and bind DNA leading to the activation of a host of inflammatory response target genes. Baldwin, A., Jr., (1996) *Annu Rev Immunol* 14: 649–683, Ghosh, S. et al, (1998) *Annu Rev Immunol* 16, 225–260. Recent evidence has shown that NF-κB subunits dynamically shuttle between the cytoplasm and the nucleus but a dominant acting nuclear export signal in IκBα ensures their transport back to the cytoplasm.

Even though NF-κB is largely considered to be a transcriptional activator, under certain circumstances it can also be involved in directly repressing gene expression (reviewed in Baldwin, A., Jr., (1996) *Annu. Rev. Immunol.*, 14: 649–683; Ghosh, S. et al. (1998) *Annu. Rev. Immunol.*, 16: 225–260).

The phosphorylation of IκB is a major triggering event in regulation of the NF-κB pathway. Since the abnormal regulation of the NF-κB pathway is known to correlate with inflammatory disease, the regulation of IκB phosphorylation is understood as an important area for disease intervention. The search for the kinase responsible for the inducible phosphorylation of IκB has been one of the major focuses in the NF-κB field. IκB phosphorylation is mediated by a high molecular weight signalsome complex consisting of at least three components: two IκB kinases IKKα, IKKβ and a non-catalytic regulatory subunit NEMO (reviewed in Mercurio, F. et al, (1999) *Oncogene*, 18: 6163–6171; Barkett, M. et al, (1999) *Oncogene*, 18: 6910–6924; Karin, M., (1999) *Oncogene*, 18: 867–6874). A great deal of study has been performed to determine the respective roles that each of the components play in the regulation of NF-kB with the belief that a greater understanding of the roles might lead to the development of new methods and approaches for the treatment of inflammatory diseases. Two molecules of NEMO are believed to orchestrate the assembly of the IKKs into the high molecular weight signalsome complex at least in part by binding to specific carboxy-terminally conserved residues of both IKKα and IKKβ termed the NEMO binding domain or NBD. Krappmann, D. et al, (2000) *J. Biol Chem* 275: 29779–29787; Li, X. H. et al, (2001) *J. Biol. Chem.*, 276: 4494–4500; Hatada, E. N. et al, (2000) *Current Opinion in Immunology*, 12: 52–58; May, M. J. et al, (2000) *Science*, 289: 1550–1554. NEMO may also facilitate the recruitment of IκBα to the IKK complex. Yamamoto, Y. et al, (2001) *J. Biol. Chem.*, 276: 36327–36336. The two catalytic IKK subunits differentially respond via NEMO to an array of signal induced, upstream kinase activities culminating in the coordinated phosphorylation of a pair of serines in their MAPK-like T activation loops by an unknown mechanism.

The roles of the IKKs in NF-κB activation were studied in mice lacking IKKβ, IKKα or NEMO. Li, Q. et al, (1999) *Science*, 28: 321–325; Li, Z. et al (1999) *J. Exp. Med.* 189: 1839–1845; Tanaka, M. et al, (1999) *Immunity* 10: 421–429; Li, Q. et al, (1999) *Genes Dev*, 13: 1322–1328; Hu, Y. et al. (1999) *Science* 284: 316–320; Takeda, K. et al, (1999) *Science* 284: 313–316. Akin to mice genetically deficient for the NF-κB p65 subunit (Beg, A. A. et al, (1995) *Nature* 376: 167–170), murine embryos genetically null for either IKKβ or NEMO succumbed to severe liver apoptosis in utero due to a virtually complete block in NF-κB activation. Li, Q. et al, (1999) *Science* 284: 321–325; Li, Z. et al, (1999) *J. Exp. Med*, 189: 1839–1845; Tanaka, M. et al, (1999) *Immunity* 10: 421–429; Rudolph, D. et al, (2000) *Genes and Dev* 14: 854–862; Schmidt-Supprian, M. et al, (2000) *Mol. Cell* 5: 981–992; Makris, C. et al, (2000) *Mol. Cell* 5: 969–979. These IKKβ and NEMO KO animals were severely if not completely deficient for both cytokine mediated IκB degradation and nuclear NF-κB DNA binding activity. Li, Q. et al, (1999) *Science* 284: 321–325; Li, Z. et al, (1999) *J. Exp. Med* 189: 1839–1845; Tanaka, M. et al, (1999) *Immunity* 10: 421–429; Rudolph, D. et al. (2000) *Genes and Dev*, 14: 854–862; Schmidt-Supprian, M. et al, (2000) *Mol. Cell* 5: 981–992; Makris, C. et al, (2000) *Mol. Cell* 5: 969–979.

In contrast, to the IKKβ and NEMO KO mice, IKKα null animals died perinatally due to severe skin, limb and skeletal abnormalities caused by a block in the terminal differentiation of epidermal kerotinocytes. Li, Q. et al, (1999) *Genes Dev* 13: 1322–1328; Hu, Y. et al, (1999) *Science* 284: 316–320; Takeda, K. et al. (1999) *Science* 284: 313–316. Subsequent work revealed that IKKα, (independent of both its kinase activity and NF-κB), controls the production of a soluble factor that induces kerotinocyte differentiation. Hu, Y., Baud, V. et al, (2001) *Nature* 410: 710–714. Furthermore, IKKα null embryos appeared to be phenotypically normal for both cytokine induced IκBα degradation, NF-κB nuclear translocation and NF-κB DNA binding activity. Hu, Y. et al, (1999) *Science* 284: 316–320; Takeda, K. et al, (1999) *Science* 284: 313–316. In addition, an independent study in cultured mammalian cells employing transfection conditions that avoided over-expression artifacts concluded that the cytokine controlled activation of NF-κB induction was an in vivo function of IKKβ and not IKKα. Delhase, M. et al, (1999) *Science* 284: 309–313.

This body of work has led to the well-accepted belief in the art that IKKβ alone is essential for NF-κB activation by inflammatory response mediators. Karin, M. (1999) *Oncogene* 18: 6867–6874; Hatada, E. N. et al, (2000) *Current Opinion in Immunology* 12: 52–58; Karin, M. et al. (2000) *Annu. Rev. Immunol* 18: 621–663. More recently and in keeping with its separate and distinct functions from IKKβ, IKKα has been shown to possess at least two additional novel in vivo functions: (a) it is essential for B lymphocyte maturation (Kaisho, T. et al, (2001) *J. Exp. Med* 193: 417–426) and Peyers patch formation via an LTβR and NIK dependent signaling pathway (Matsushima, A. et al, (2001) *J. Exp. Med* 193: 631–636), wherein it is required to target the cytokine induced processing of the NF-κB2 (p100) precursor to produce the functional NF-κB p52 subunit (Senftleben, U. et al, (2001) *Science* 293: 1495–1499) and (b) it is required for the proliferation of mammary epithelial cells in response to RANK ligand but not TNFα signaling to activate cyclin D1. Cao, Y., Bonizzi, G. et al, (2001) *Cell* 107: 763–775. Independent of these studies, IKKβ was reported to phosphorylate an IκB-like destruction motif in p50's p105 precursor, which produces a recognition site for βTrCP-containing SCF ubiquitin ligases with subsequent polyubiquination of p105 causing its complete proteasomal destruction and the induced release of DNA binding p50 homodimers (Heissmeyer, V. et al, (1999) *Embo. J,* 18: 4766–4778; Heissmeyer, V. et al, (2001) *Mol. Cell Biol,* 21: 1024–1035), providing additional support for the notion that IKKβ and IKKα have distinct roles in NF-κB activation.

In addition to the well accepted belief of induced nuclear translocation of NF-κB dependent gene expression, an alternative mechanism has emerged that involves the phosphorylation of the p65 transactivation subunit. The protein kinase A catalytic subunit phosphorylates p65 which leads to the association of p65 and the p300 transcriptional coactivator. Zhong, H. et al, *Mol. Cell.,* (1998) 1: 661–671. Cells from GSK3 and T2K knockout mice are capable of inducing NF-κB nuclear translocation but are deficient in stimulating transactivation functions of NF-κB. Hoeflich et al, (2000) *Nature* 406: 86–90; Bonnard, M. et al, (2000) *Embo. J,* 19: 4976–4985. Thus, NF-κB dependent gene transcription is regulated at other step(s) in addition to IκBα degradation and NF-κB translocation.

Recently, it has been shown that in mouse embryonic fibrolasts, IKKα is required for NF-κB-mediated gene transcription in response to proinflammatory cytokine TNFα and IL-1β. Li, X. et al, (2002) *J. Biol. Chem,* 277: 45129–45140. This is in dramatic contrast to the generally accepted view of IKKα being dispensable for TNF and IL-1 induced gene transcription mediated by NF-κB. Hu, Y. et al, (1999) *Science* 284: 316–320; Takeda, K. et al, (1999) *Science* 284: 313–316. One way to demonstrate that IKKα is also needed for TNFα—induced NF-κB dependent gene transcription in human cells, is to specifically knock down the expression or activity of IKKα.

The function of a gene can be determined on the basis of the behavior of cells in which the level of gene expression or level of activity of the gene product has been reduced. Experimental procedures can be used to specifically inactivate or silence a target gene or inhibit the activity of its gene product. Inhibition of protein activity can be brought about at the level of gene transcription, protein translation or post translational modifications. For instance, the activity of a protein can be inhibited by directly inhibiting the activity of the protein such as altering a catalytic domain or alternatively by reducing the amount of the protein in the cell by reducing the amount of mRNA encoding the protein. In each case the level of protein activity in the cell is reduced. Various techniques can be used to knock down the activity of a protein and these include knockout technologies (antibodies, antisense RNA, and RNA interference) and compounds that specifically inhibit the protein activity. Antisense RNAs directed to IKKα has been reported for use in the inhibition of IKKα expression. U.S. Pat. No. 6,395,545.

It is anticipated that compounds capable of modulating the expression of IKKα, and/or modulating the activity of IKKα may provide for a novel class of agents with activity toward a variety of inflammatory and autoimmune diseases such as osteoarthritis, reperfusion injury, asthma, multiple sclerosis, Guillain-Barre syndrome, Crohn's disease, ulcerative colitis, psoriasis, graft versus host disease, systemic lupus erythematosus, rheumatoid arthritis, Alzheimer's disease, toxic shock syndrome, inflammatory bowel disease, insulin-dependent diabetes mellitus, acute and chronic pain as well as symptoms of inflammation and cardiovascular disease, stroke, myocardial infarction alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis.

RNA interference (RNAi) is a technique that can be used to knockdown the activity of genes and their protein products in a specific manner. RNAi was first used in the Nematode worm *Caenorhabditis elegans* as a response to double stranded RNA (dsRNA) that resulted in the gene knockdown specific manner. Fire, A. et al, (1998) *Nature* 391: 806–811. RNAi is a process whereby a double stranded RNA (dsRNA) of a sequence that is homologous to a target gene can be used to cause the degradation of messenger RNA (mRNA) transcribed from that target gene. Sharp, P. A., (2001) *Genes Dev,* 15: 485–490. Initiation of gene silencing or gene inactivation occurs upon recognition of dsRNA by the cells machinery that convert the silencing trigger to 21–25 nucleotides RNAs. Hannon, (2002) *Nature* 418: 244–250.

The mediators of sequence-specific messenger RNA degradation are 21- and 22-nucleotide small interfering RNAs (siRNAs) generated by ribonuclease III cleavage from longer dsRNAs. In vitro synthesized 21-nucleotide siRNA duplexes specifically suppress expression of endogenous and heterologous genes in different mammalian cell lines, including human embryonic kidney and HeLa cells. Elbashir S. et al, (2001) *Nature,* 411: 494–498. Therefore, 21-nucleotide siRNA duplexes provide a new tool for studying gene function in mammalian cells and may be used as gene-specific therapeutics. However, effective gene silencing is only caused by a subset of siRNAs complementary to the mRNA target. McManus MT et al, (2002) *J. Immunol* 169: 5754–60. Thus, design of multiple siRNA oligos and extensive testing are required to obtain a potent siRNA oligo. McManus MT et al, (2002) *J. Immunol* 169: 5754–60.

The ability to specifically knock down expression of a target gene by si RNA has many benefits. For example si RNA could be used to mimic true genetic knockout animals to study gene function. There have been reports of using siRNA for various purposes including the inhibition of luciferase gene expression in human cells, (see US Patent Application No. 2002/0132788); HIV-1 Cellular receptor CD4 (Sharp et al, (2002) *Nature Medicine* 8: 681–686); HIV accessory genes, vif and nef (Nature Advance Online Publication, Jun. 26, 2002 (doi: 10.1038/nature 00896); HPV E6 and E7 gene expression. Jiang M., *Oncogene,* (2002), 21:6041–6048); Subtype- and species-specific knockdown of protein kinase C (Irie N. et al, *Biochem. Biophys. Res. Commun.*, (2002) 298: 738–743.

BRIEF SUMMARY OF THE INVENTION

A first embodiment of the invention provides a method for modulating NF-κB dependent gene transcription in a cell, said method comprised of modulating IKKα activity in the cell.

A second embodiment of the invention provides for selectively modulating expression of a gene whose transcription is regulated by IKKα, the method comprising modulating IKKα activity such that expression of the gene is modulated.

A third embodiment of the invention provides for modulating NF-κB dependent gene transcription by administration of siRNA directed to IKKα to cells. SiRNA can be 21 to 25 nucleotides in length and hybridize to a nucleic acid molecule encoding human IKKα.

A fourth embodiment of the invention provides a method for treating autoimmune and inflammatory disease in a mammal wherein the method is comprised of modulating IKKα expression or IKKα activity.

A fifth embodiment of the invention provides a method for treating autoimmune and inflammatory disease in a mammal wherein the method is comprised of modulating IKKα expression or IKKα activity by administration of siRNA directed to IKKα.

A sixth embodiment of the invention provides a method for reducing the effects of TNFα induced genes in cells, the method comprised of reducing IKKα activity in a cell.

A seventh embodiment of the invention provides a method for reducing the effects of NF-κB induced gene transcription, the method comprised of reducing IKKα activity in a cell.

An eighth embodiment of the invention provides a siRNA composition that when administered to a cell modulates IKKα activity.

A ninth embodiment of the invention provides a method for identifying a compound for the treatment of autoimmune and inflammatory disease, said method comprised of the steps of:
1) incubating an IKKα protein in the presence of a potential inhibitor of IKKα activity;
2) measuring the loss of IKKα activity;
3) comparing the amount of IKKα activity present in the absence of a potential inhibitor.

Either the fully encoded IKKα or a fragment thereof can be used in the method for identifying a compound for the treatment of autoimmune and inflammatory disease.

One particular advantage of using inhibitors specific to IKKα in the present invention is that such inhibitors may have less side effects such as liver apoptosis as compared to inhibitors for IKKβ and NEMO. Other features and advantages of the invention will be apparent from the following detailed description of the invention.

DETAILED DESCRIPTION OF THE INVENTION

I. General Description

Figure 1:
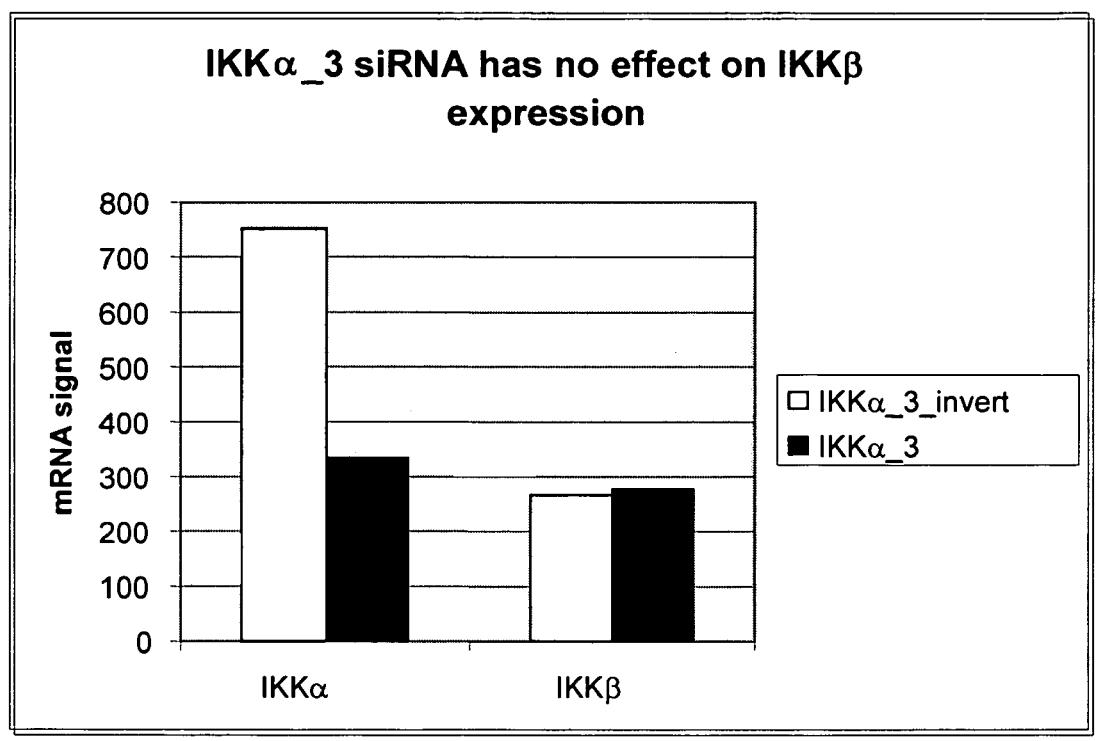
FIG. 1 shows the effect of IKKα and IKKβ mRNA expression in HeLa cells after administration of siRNA directed to IKKα.

The present invention provides a method for modulating NF-κB dependent gene transcription, said method comprised of the step of modulating IKKα protein activity in a cell. The level of IKKα protein activity in a cell can be modulated upward or downward. The level of IKKα activity is preferentially modulated downward. One embodiment of the invention is based in part on the demonstration that the use of an IKKα specific inhibitor in TNFα stimulated human cells results in the modulation of genes under the influence of NF-κB.

The present invention employs siRNA for use in modulating the level of IKKα protein activity in the cell. SiRNA oligonucleotides directed to IKKα specifically hybridize nucleic acids encoding IKKα and interfere with IKKα gene expression. Accordingly, IKKα proteins levels are reduced and the total level of IKKα activity in the cell is reduced. Since IKKα has been shown to play a role in triggering the NF-κB pathway (Table I; Li, X. et al, (2002) *J. Biol. Chem*, 277: 45129–45140), which functions in the inflammatory response, compounds that have the property of being able to specifically and effectively inhibit IKKα are understood to be helpful in the treatment of autoimmune and inflammatory diseases.

Without intending to be limited by mechanism, it is believed that an IKKα specific inhibitor acts by reducing the amount of activity of IKKα protein and or IKKα expression in a cell, thereby directly or indirectly reducing the phosphorylation of NF-κB p100 Pomerantz, J. L. and Baltimore, D., *Mol. Cell*, (2002) 10:693–5) or NF-κB p65. Sizemore, N. et al, *J. Biol. Chem.*, (2002) 277: 3863–9.

The present invention also provides methods for treating inflammatory and autoimmune diseases using inhibitors of IKKα activity and is based in part on the demonstration that the expression of proinflammatory genes under the influence of the NF-κB pathway can be inhibited upon administering IKKα specific inhibitors to a cell. NF-κB dependent genes are found to be over expressed in autoimmune and inflammatory conditions. Barnes et al, (1997) *New England J. Med*, 336: 1066–1071; US 2002/0156000; U.S. Pat. Nos. 6,395,545; 6,440,973; WO 02/060386 incorporated herein by reference.

The present invention also provides methods for identifying compounds that modulate the activity of IKKα for the treatment of autoimmune and inflammatory disease.

Definitions:

Unless defined otherwise, the scientific and technological terms and nomenclature used herein have the same meaning as commonly understood by a person of ordinary skill in the art to which this invention pertains.

Nucleotide sequences are presented herein by a single strand, in the 5' to 3' direction, from left to right, using the one letter nucleotide symbols as commonly used in the art and according with the recommendations of the IUPAC-IUB Biochemical Nomenclature Commission (1972).

The term "IKKα" as it is used herein refers to the alpha subunit of the IκB kinase complex. IKKα is a kinase that phosphorylates IκB, NF-κB p100 or other protein substrates.

The term "gene transcription" as it is used herein means a process whereby one strand of a DNA molecule is used as a template for synthesis of a complementary RNA by RNA polymerase.

The term "DNA" as used herein refers to polynucleotide molecules, segments or sequences and is used herein to refer to a chain of nucleotides, each containing the sugar deoxyribose and one of the four adenine (A), guanine (G) thymine (T) or cytosine (C).

The term "RNA" as used herein refers to polynucleotide molecules, segments or sequences and is used herein to refer to a chain of nucleotides each containing the sugar ribose and one of the four adenine (A), guanine (G) uracil (U) or cytosine (C).

The term "oligo" as used herein means a short sequence of DNA or DNA derivatives typically 8 to 35 nucleotides in length. An oligonucleotide can be derived synthetically, by cloning or by amplification. The term "derivative" is intended to include any of the above described variants when comprising an additional chemical moiety not normally a part of these molecules. These chemical moieties can have varying purposes including, improving solubility, absorption, biological half life, decreasing toxicity and eliminating or decreasing undesirable side effects.

The term "specifically hybridize" as used herein means that under appropriate conditions a probe made or a nucleic acid sequence such as an siRNA oligo hybridizes, duplexes or binds only to a particular target DNA or RNA sequence present in a cell or preparation of DNA or RNA. A probe sequence such as an siRNA sequence specifically hybridizes to a target sequence when the base sequence of the probe nucleic acid and the target sequence are complimentary to one another. The target sequence and the probe sequence do not have to be exactly complimentary to one another in order for the probe sequence to specifically hybridize. It is understood that specific hybridization can occur when the target and probe sequences are not exactly complimentary to one another and specific hybridization can occur when up only about 80% of the bases are complimentary to one another. Preferably, it is understood that in specific hybridizations probe and target sequence have 80% comprehensibility to one another. For discussions on hybridization see for example, Current Protocols in Molecular Biology, F. Ausubel et al., (ed.) Greene Publishing and Wiley-Interscience, New York (July, 2002).

The term "RNAi" as used herein means RNA interference process for a sequence-specific post-transcriptional gene silencing or gene knockdown by providing a double-stranded RNA (dsRNA) that is homologous in sequence to the targeted gene. Small interfering RNAs (siRNAs) can be synthesized in vitro or generated by ribonuclease III cleavage from longer dsRNA and are the mediators of sequence-specific mRNA degradation.

The term "modulating IKKα activity" as used herein means either inhibiting (decreasing) or stimulating (increasing) the level of activity of IKKα protein in a cell. IKKα activity can be modulated by modification of the levels and/or activity of IKKα protein, or by modification of the level of IKKα gene transcription and/or IKK 2 activity structure such that the levels of IKKα protein activity in the cell is modulated. In the context of the present invention, inhibition is the preferred form of modulation.

The term "autoimmune and inflammatory disease" as used herein means diseases that are associated with autoimmune and inflammatory conditions such as inflammatory and autoimmune conditions such as osteoarthritis, reperfusion injury, asthma, multiple sclerosis, Guillain-Barre syndrome, Crohn's disease, ulcerative colitis, psoriasis, graft versus host disease, systemic lupus erythematosus, rheumatoid arthritis, Alzheimer's disease, toxic shock syndrome, insulin-dependent diabetes mellitis, acute and chronic pain as well as symptoms of inflammation and cardiovascular disease, stroke, myocardial infarction alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, Grave's disease, myasthenia gravis, scleroderma and atopic dermatitis.

The term "protein fragment" as used herein means a truncated form of a protein. For IKKα suitable protein fragments should include the kinase domain understood as extending from at least amino acid residues 15 to 293 (SEQ. ID No. 2).

The term "protein" as used herein means isolated naturally occurring polypeptides, recombinantly produced proteins. Means for preparing such proteins are well understood in the art. Proteins may be in the form of the secreted protein, including truncated or mature forms. Proteins may optionally be modified to include an additional amino acid sequence which contains secretory or leader sequences, pro-sequences, sequences which aid in purification, such as multiple histidine residues, or an additional sequence for stability during recombinant production. The proteins of the present invention are preferably provided in an isolated form, and preferably are substantially purified. A recombinantly produced version of a protein, including the secreted protein, can be substantially purified using techniques described herein or otherwise known in the art, such as, for example, by the one-step method described in Smith et al, *Gene* 67:31–40 (1988). Proteins of the invention also can be purified from natural, synthetic or recombinant sources using techniques described herein or otherwise known in the art.

The term "Gene knockdown" as used herein refers to the reduction in the activity of a gene. The term "gene silencing" or gene inactivation are considered to have the same meaning as the terms are used herein.

The term "potential inhibitor of IKKα activity" as used herein means any compound or molecule that can cause the inhibition of IKKα activity. The inhibition of IKKα activity should be specific to IKKα. Potential IKKα inhibitors can be compounds that block, antagonize, prevent, or reduce the activation of IKKα. IKKα inhibitors inhibit the activity of IKKα, preferably the in vivo activity, such that the catalytic activity of IKKα is inhibited 2) the phosphorylation of p100 or NF-κB, p65 or IκB is inhibited or 3) NF-κB dependent proinflammatory genes are inhibited. SiRNA as well as small molecule inhibitors directed to IKKα can be potential inhibitors of IKKα activity.

The term "proinflammatory gene" as used herein refers to any gene that is induced upon an inflammatory response through the NF-κB pathway. Examples of proinflammatory genes include but are not limited to beta inhibin, IL-8, IL-6, interferon stimulated protein, TNF-induced protein, Cox2, GRO1 oncogene, CD44, interleukin 11, and superoxide dismutase.

The term "specific inhibitor" as used herein means an inhibitor that inhibits one protein more than another protein. For example, a potential inhibitor of IKKα is considered to be specific for IKKα over another IKKβ protein when there is preferably at least 10 to 100 fold or greater and most preferably about 1000 fold difference in inhibition of IKKα compared to IKKβ.

The term "NF-κB gene transcription" as used herein means genes that are either upregulated or downregulated in response to the level of NF-κB activity in a cell. Such genes include, but are not limited to IL-6, IL-8, inhibin, beta A, intercellular adhesion molecule 1, interferon stimulated protein, Cox2, IL-11, GRO1 and superoxide dismutase. NF-κB dependent genes are also discussed in US 2002/0156000: Barnes et al. (1997) *New England J. Med* 336: 1066–1071; Pahl H L, Oncogene, (1999), 18, 6853–6866 incorporated herein by reference.

The term "delivery" as used herein refers to the introduction of foreign molecule (i.e. nucleic acid small molecule inhibitor) in cells.

The term "treating" as used herein means the prevention, reduction, partial or complete alleviation or cure of a disease.

Using the present invention it is possible to observe the function of IKKα. In addition, specific siRNA oligos directed to IKKα have been designed and tested in human cells showing a reduction in the expression of proinflammatory genes and NF-κB target genes with their use. These siRNA and equivalent compounds may have therapeutic value in the treatment of autoimmune and inflammatory disease as described herein. It is therefore understood that compounds that inhibit either IKKα expression or IKKα protein activity also have therapeutic value.

The term "Administration" as used herein means the introduction of a Foreign molecule (i.e. nucleic acid, small molecule inhibitor) into a cell. The term is intended to be synonymous with the term "Delivery".

III. Specific Embodiments

Preferred aspects of embodiments of the present invention are described in the following examples, which are not to be construed as limiting.

In one embodiment the method of the invention is used to reduce NF-κB dependent gene expression in a cell, said method comprised of reducing IKKα protein activity in a cell. The level of NF-κB dependent gene expression is proportionate to the level of IKKα activity in the cell. In other words, when the level of IKKα activity is lowered the level of expression of proinflammatory NF-κB dependent genes is also reduced.

The method of the invention can comprise modulating NF-κB dependent gene expression in a cell by administration of siRNA directed to IKKα. RNA interference is a method whereby siRNA can be used to knockdown or reduce the level of expression of a specific gene. In the case of IKKα, siRNA specifically directed to IKKα can be administered to cells in order to knockdown IKKα protein activity in the cell and to reduce the expression of NF-κB proinflammatory genes. SiRNA can be designed according to the technique described by Tuschl, described as follows. Elbashir, S M et al, Nature, 2001, 411, 494–498. SiRNA that can efficiently knockdown a gene can be obtained by using siRNA duplexes composed of 21 nt sense and 21 nt antisense strands paired in a manner to have a 2-nt 3' overhang. The sequence of the 2-nt overhang is thought to make a contribution to the specificity of the target recognition restricted to the unpaired nucleotide adjacent to the first base pair. 2-Deoxynucleotides are used in the 3' overhang.

The targeted region is selected from the human cDNA beginning at about 100 nt downstream of the start codon. Sequences can be searched for AA(N19)TT with approximately 40–60% G/C content. AA(N19) should match exactly the sequence of sense cDNA. The sequence of the sense siRNA corresponds to (N19)TT or N21, respectively. N19 exactly matches the sequence of sense cDNA. A blast search should be performed on the selected siRNA against genebank full-length genes and ESTs to ensure that only one gene is targeted. The sequence of the siRNA should be selective to the target sequence.

Preparation of the siRNA Duplexes

The siRNA duplexes used for delivery to cells can be prepared as follows. Approximately 0.02 to 0.2 µM of the synthetic siRNAs can be used for delivery to various types of cells such as HeLa cells, Jurkat T cells, lymphocytes, HUVEC cells and fibroblasts. SiRNAs can be obtained from a number of sources including Dharmacon (Lafayette, Colo.) and Ambion (Austin, Tex.). The siRNA can be prepared by synthesizing the sense and antisense strand 21-nt oligos, followed by annealing of the single standed oligos. The siRNA can be incubated, pelleted and quantified using UV spectroscopy methods understood and used in the art.

Delivery of siRNA to Cells and Transfection of siRNA Duplexes

Delivery of siRNA to cells can be performed according to cell transfection methods commonly used in the art. Elbashir S M et al, *Nature* 2001, 411, 494–498; McManus MT et al, *J. Immunol* 2002 ,169:5754–60; Barton G M et al, *Proc. Natl. Acad. Sci.* (2002) 99:14943–5. Delivery of siRNA can be performed on various types of tissue culture cells. Preferably tissue culture cells of autoimmune or inflammatory significance such as lymphocytes, epithelium cells and endothelial cells should be used. More specifically cells such as HeLa cells, Jurkat T cells, lymphocytes, HUVEC cells and fibroblasts. SiRNA can be delivered to tissue and organisms as well. Lewis D L et al, *Nat. Genet.* (2002) 32:107–8; McCaffrey A P et al, *Nature* (2002) 418:38–39.

Various transfection reagents can be used for siRNA delivery such as lipids-mediated transfection, electroporation or virus. In the preferred method the transfection reagent is OLIGOFECTAMINE™ available from Invitrogen (Carlsbad, Calif.). Transfection efficiencies should be between 40 and 100%.

For each sample between about 1 to 10 µg of siRNA duplex and about 100 µl of Opti-MEM are mixed. In a separate tube 1 volume of Oligofectamine and 4 volumes of Opti-MEM are incubated from about 10 to 15 minutes at room temperature. The samples are then mixed and incubated for another 20 to 25 minutes at room temperature. Then 16 volumes of fresh Opti-MEM is added. SiRNA-transfection reagent is added to cultured cells (40 to 50% confluent). The cells are seeded for about 24 hours prior in antibiotics-free medium using culture techniques commonly used in the art.

A knockdown effect should be found between 1 to 5 days after delivery of the siRNA. The amount of knockdown is generally 40 to 100% of normal mRNA levels, and most preferably 60 to 100% of normal mRNA levels.

Treatment of Cells with a Proinflammatory Agent

In order to measure the extent of inhibition of NF-κB dependent proinflammatory genes, proinflammatory agents are administered to the cell. Acceptable proinflammatory agents are compounds that induce expression of proinflammatory genes under the NF-κB pathway. Proinflammatory agents include but are not limited to TNFα, IL-1 and LPS. The preferred proinflammatory agent is TNFα. It is understood that other proinflammatory agents may effect expression of NF-κB dependent genes. The stimulation time and the amount of proinflammatory agent that is used will vary according to the agent used but will be an amount sufficient to elicit a measurable proinflammatory response. TNFα is added to the cells with about 1 to 10 ng/ml for 30 minutes to 24 hours. Typically, the proinflammatory agent is added before the measurement of proinflammatory genes is taken.

Preparation of RNA and PCR Primers

The level of gene knockdown or inhibition of gene transcription can be measured by analysis of mRNA from total RNA samples. Total RNA can be prepared between about 24 and 72 hrs after delivery siRNA using methods known to those skilled in the art. Preferably total cellular RNA is isolated from tissue or cell samples using the RNeasy™ kit and Rnase-Free DNase Set Protocol from Qiagen (Valencia, Calif.) according to the manufacturer's description.

TaqMan Real-Time PCR Procedures

PCR analysis can be used to analyze the isolated RNA and quantify the effects of the IKKα inhibitor on the transcription of NF-κB dependent genes. PCR primers and/or probes used for the measurement of the transcription level of these genes can be prepared using techniques that are commonly used in the art. PCR primers should be designed for the amplification of the cDNA sequence from genes of interest. Software can be used to assist in designing design primers specific for target genes. Preferred software is Primer Express 1.5 Software (Applied Biosystems (Foster City, Calif.). Probes can be labeled with reporter agents such as fluorescent dye, FAM (6-carboxyfluorescein) at the 5' end and a fluorescent dye quencher TAMRA (6-carboxy-tetramethyl-rhodamine) at the 3' end. Other reporter agents commonly used in the art such as $P^{32}$, $S^{35}$ fluorescein and Biotin can also be used. The specificity of PCR primers can be tested under normal PCR conditions in a thermal cycler prior to PCR quantitation. Total cellular RNA isolated from tissue or cell samples are used in reverse transcription (RT) reactions.

A "standard curve" can be constructed by plotting the $C_t$ vs. the known copy numbers of the template in the standard. According to the standard curve, the copy numbers for all unknown samples are obtained automatically. To determine the copy numbers of the target transcript, a human genomic DNA (Clontech (Palo Alto, Calif.) can be used to generate a standard curve. The copy numbers of genomic DNA template are calculated according to the molecular weight of human diploid genome [$3 \times 10^9$ bp=$3 \times 10^9 \times 660$ (M.W.)=$2 \times 10^{12}$ g], and then 1 µg/µl genomic DNA is converted into $2.4 \times 10^6$ copy numbers based upon the Avogadro's number (1 mol=$6.022 \times 10^{23}$ molecules). Serial dilutions of the samples can be run in order to establish an estimate of the copy numbers. Copy numbers can be normalized to GAPDH or other housekeeping genes to minimize variability in the results due to differences in the RT efficiency and RNA integrity among test samples.

Microarray Studies

Analysis of the transcription levels of genes can also be performed using microarray or cRNA chip analysis. These technologies allow the analysis of multiple genes in a single experiment. Preparation of cRNA, hybridization are performed according to methods as described herein and as otherwise commonly used in the art. Microarray analysis can be performed using procedures available from various companies such as Affymetrix and Agilent technologies.

The Affymetrix procedure is the preferred method and is performed essentially as follows: Between 5 and 10 micrograms of the total RNA can be converted into double stranded cDNA by reverse transcription using a cDNA synthesis kit. The preferred kit for cDNA synthesis is Superscript Choice™, Invitrogen (Carlsbad, Calif.)) which has a special oligo (dT)24 primer (Genset, La Jolla, Calif.) containing a T7 RNA polymerase promoter site added 3' of the poly T tract. After second strand synthesis, labeled cRNA is generated from the cDNA samples by an in vitro transcription reaction using a reporting reagent such as biotin-11-CTP and biotin-16-UTP (Enzo, Farmingdale, N.Y.). Labeled cRNA can be purified by techniques commonly used in the art. The preferred method is to use RNeasy spin columns (Qiagen, Valencia, Calif.). About 10 to 3 micrograms of each cRNA sample can be fragmented by mild alkaline treatment. Preferably, the cRNA sample is fragmented by treatment at 94° C. for 35 minutes in fragmentation buffer as suggested by the manufacturer. A mixture of control cRNAs for bacterial and phage genes should be included to serve as tools for comparing hybridization efficiency between arrays and for relative quantitation of measured transcript levels. Before hybridization, the cRNA samples are heated at about 94° C. for 5 minutes, equilibrated at 45° C. for 5 minutes and clarified by centrifugation (14,000×g) at room temperature for 5 minutes. Aliquots of each cRNA sample are hybridized to arrays, according the manufacturer's directions. The arrays were then washed according to methods according to the manufacturer. The preferred wash is with non-stringent (6×SSPE, 0.01% Tween-20, 0.005% antifoam) and stringent (100 mm MES, 0.1M NaCl, 0.01% Tween 20), stained with R-Phycoerythrin Streptavidin-(Molecular Probes, Eugene, Oreg.), washed again and scanned by an argon-ion laser scanner with the 560-nm long-pass filter (Molecular Dynamics; Affymetrix, Santa Clara, Calif.). Data analysis can be performed in order to determine if a gene expression level is increased, decreased or unchanged. Preferably, software such as MAS 5.0 software (Affymetrix, Santa Clara, Calif.) is used.

Identification of IKKα Inhibitor Compounds

Another embodiment of the invention provides a method for identifying a compound for the treatment of autoimmune and inflammatory disease, said method comprised of the steps of:

1) incubating an IKKα protein in the presence of a potential inhibitor of IKKα activity;

2) measuring the loss of IKKα activity;

3) comparing the amount of IKKα activity present in the absence of a potential inhibitor.

Compounds that are inhibitors of IKKα expression or IKKα activity for use in the treatment of autoimmune and inflammatory disease can be identified using the method of the invention. IKKα activity can be measured by determining the level of phosphorylation of the IκB protein. Li, J. et al, 1998, *J. Biol. Chem.* 273:30736–41. A potential inhibitor of IKKα can be siRNA directed to IKKα or other small molecule inhibitor compounds that interact with the IKKα protein. Using the method of the invention siRNA directed to IKKα is delivered to cells according to the methods described herein or methods known in the art. In the case of siRNA inhibitors, the inhibitor compound does not have to be incubated with the IKKα protein. Compounds whose inhibitory activities are dependent on interaction with IKKα protein should be incubated with the IKKα protein. It is understood that the IKKα siRNA does not have to be incubated with the IKKα protein in embodiments for identifying compounds for the treatment of autoimmune and inflammatory disease since IKKα siRNA inhibits IKKα protein activity without interacting or contacting the IKKα protein. The method of the invention can be practiced using compounds that interact with IKKα protein and inhibit IKKα protein activity as well as using compounds that inhibit IKKα protein activity by inhibiting IKKα expression. After incubation and/or delivery of the potential inhibitor compound IKKα activity can be measured and then compared to the amount of IKKα activity present.

This invention is further exemplified by the following examples which should not be construed as limiting. The contents of all references, patents and published patent applications cited throughout this application, as well as the figures and sequence listing are hereby incorporated by reference. IKKα inhibitor compounds should be specific to IKKα. Preferably IKKα inhibitor compounds are specific for IKKα over another IKKα protein when there is at least 10 to 100 fold or greater and most preferably about 100 fold difference in inhibition of the IKKα compared to IKKβ.

The present invention also includes pharmaceutical compositions and formulations which include siRNA compounds as described herein. The pharmaceutical compositions can be administered topically, by inhalation, oral or parenteral as taught in U.S. Pat. No. 6,395,545, incorporated herein by reference. A preferred method of administration is as an emulsion or microemulsions. Another method of administration is through use of liposomal formulations. Another method of administration using a "high pressure" delivery of RNAI into mammalian organs may also be used. See Nature Genetics Vol. 32 p107–108 incorporated herein by reference.

EXAMPLE 1

Preparation of siRNA Duplexes.

SiRNA directed to IKKα sequence was designed according to the technique described by Tuschl. Elbashir S M et al, Nature 2001, 411, 494–498. SiRNA duplexes composed of 21 nt sense and 21 nt antisense strands, paired in a manner to have a 2-nt 3' overhang were used. The sequence of the 2-nt overhang is thought to make a contribution to the specificity of the target recognition restricted to the unpaired nucleotide adjacent to the first base pair. 2-Deoxynucleotides were used in the 3' overhang.

The targeted region was selected from the cDNA for human IKKα shown in SEQ. ID No. 1 beginning 100 nt downstream of the start codon. Sequences were searched for AA(N19)TT and with approximately 50% G/C content. The sequence of the sense siRNA corresponded to (N19)TT to N21, respectively. The 3' end of the sense RNA was converted to TT. A blast search was performed on the selected siRNA against EST libraries to ensure that only one gene was targeted. The sequences selected are shown as SEQ. ID Nos. 2–7.

Approximately 0.2 micromoles of the synthetic siRNAs were obtained from Dharmacon Research Inc. (Lafayette, Colo.). The siRNAs were desalted and deprotected by the supplier and therefore were not further gel purified. The siRNA oligos were annealed and shipped in 4 tubes. Each tube was added 1 ml sterile RNase-free water to make 20 μM siRNA concentrations. After 1 to 2 hours of incubation on ice the siRNAs were ready for use in transfection.

EXAMPLE 2

Delivery of siRNA to HeLa Cells

Transfection of siRNA Duplexes

Delivery of siRNA duplexes was performed with OLIGOFECTAMINE™ reagent available from Invitrogen (Carlsbad, Calif.). The samples were prepared in a 6 well format. Transfection efficiencies were found to be about 80%.

For each well of a 6 well plate, one tube containing 10 μl of 20 μM siRNA duplex with 90 μl of Opti-MEM, and in a separate tube 4 μl of OLOGOFECTAMIN™ reagent with 96 μl of Opti-MEM were mixed and incubated for 7–10 minutes at room temperature. The two tubes were combined and incubated for another 20 to 25 minutes at room temperature. Then 800 μl of fresh Opti-MEM was added to obtain a final solution of 1000 μl. Then 1000 μl of siRNA-OLIGOFECTAMINE™ was added to cultured cells (40 to 50% confluent). The cells were seeded the previous day in 6-well plates at a density of $2\times10^5$ cells/well using 2 ml of DMEM tissue culture medium supplemented with 10% FBS without antibiotics. The control used for transfection was inverted siRNA. A knockdown effect was generally found after 1–2 days.

EXAMPLE 3

Preparation of RNA and PCR Primers

Total RNA was prepared from the cells 2 days after delivery of siRNA's. Total cellular RNA was isolated from tissue or cell samples using the RNeasy™ kit and Rnase-Free DNase Set Protocol from Qiagen (Valencia, Calif.) according to the manufacturer's directions. PCR primers and TaqMan probes were designed using Primer Express 1.5 Software (Applied Biosystems, Foster, Calif.). The sequence of the PCR primers used were SEQ. ID. No. 9: 5'-GCACA-GAGATGGTGAAAATCATTG-3', and SEQ. ID. No. 10: 5'-CAACTTGCTCAAATGACCAAACAG-3'. The probe sequence SeQ. ID No. 11: 5'-TGAGCACACGGTCCT-GACTCTGCA labeled with a reporter fluorescent dye, FAM (6-carboxyfluorescein), at the 5' end and a fluorescent dye quencher TAMRA (6-carboxy-tetramethyl-rhodamine) at the 3' end. The specificity of PCR primers was tested under normal PCR conditions in a thermal cycler prior to Taq-Man™ PCR quantitation. Total cellular RNA was isolated from cell samples using the RNeasy Kits and RNase-Free DNase Set Protocol according to the manufacturer's description (Qiagen). Reverse transcription (RT) reactions were carried out for each RNA sample in MicroAmp reaction tubes using TaqMan™ reverse transcription reagents. Each reaction tube contained 500 ng of total RNA in a volume of 50 μl containing 1×TaqMan™ RT buffer, 5.5 mM $MgCl_2$, 500 μM of each dNTP, 2.5 μM of Random Hexamers or oligo-d(T)$_{16}$ primers, 0.4 U/μl of RNase inhibitor, and 1.25 U/μl of MultiScribe Reverse Transcriptase. RT reactions were carried out at 25° C. for 10 min, 48° C. for 40 min and 95° C. for 5 min. Real-time PCR was performed in a MicroAmp Optical 96-Well Reaction Plate (Applied Biosystems). Each well contained 2 μl of each RT product (20 ng total RNA), 1×TaqMan buffer A, 5.5 mM $MgCl_2$, 200 μM dATP/dCTP/dGTP, 400 μM dUTP, 200 nM primers (forward and reverse), 100 nM TaqMan™ probe, 0.01 U/μl AmpErase, and 0.025 U/μl AmpliTaq™ Gold DNA polymerase in a total volume of 25 μl. Each well was closed with Micro-Amp Optical caps (Applied Biosystems), following complete loading of reagents. Amplification conditions were 2 min at 50° C. (for AmpErase UNG incubation to remove any uracil incorporated into the cDNA), 10 min at 95° C. (for AmpliTaq™ Gold activation), and then run for 40 cycles at 95° C. for 15 s, 60° C. for 1 min. All reactions were performed in the ABI Prism 7700 Sequence Detection System for the test samples, standards, and no template controls. They were run in triplicates using the Sequence Detector V 1.6 program. The $R_n$ and $C_t$ were averaged from the values obtained in each reaction. A "standard curve" was constructed by plotting the $C_t$ vs. the known copy numbers of the template in the standard. According to the standard curve, the copy numbers for all unknown samples were obtained automatically. To determine the copy numbers of the target transcript, a human genomic DNA (Clontech, Palo Alto, Calif.) was used to generate a standard curve. The copy numbers of genomic DNA template were calculated according to the molecular weight of human diploid genome [$3 \times 10^9$ bp=$3 \times 10^9 \times 660$ (M.W.)=$2 \times 10^{12}$ g], and then 1 µg/µl genomic DNA was converted into $2.4 \times 10^6$ copy numbers based upon the Avogadro's number (1 mol=$6.022 \times 10^{23}$ molecules). The genomic DNA was serially (every ten-fold) diluted at a range of $5 \times 10^5$ to $5 \times 10^0$ copy numbers. Each sample was run in triplicates, and the $R_n$ (the ratio of the amount of reporter dye emission to the quenching dye emission) and threshold cycle ($C_t$) values were averaged from each reaction. The copy numbers were then normalized to GAPDH to minimize variability in the results due to differences in the RT efficiency and RNA integrity among test samples.

EXAMPLE 4

Microarray Studies Using Affymetrix

Preparation of cRNA and Gene Chip Analysis.

Preparation of cRNA, hybridization and scanning of the U133A were performed according to the manufacturer's protocol (Affymetrix, Santa Clara, Calif.). Briefly, 5–10 µg of the total RNA was converted into double stranded cDNA by reverse transcription using a cDNA synthesis kit (Superscript Choice™, Invitrogen Carlsbad, Calif. with a special oligo(dT024 primer) (Genset, La Jolla, Calif.) containing a T7 RNA polymerase promoter site added 3' of the poly T tract. After second strand synthesis, labeled cRNA was generated from the cDNA samples by an in vitro transcription reaction supplemented with biotin-11-CTP and biotin-16-UTP (Enzo, Farmingdale, N.Y.). The labeled cRNA was purified by using RNeasy spin columns (Qiagen, Valencia, Calif.). Fifteen micrograms of each cRNA sample was fragmented by mild alkaline treatment at 94° C. for 35 minutes in fragmentation buffer (40 mM Tris-acetate, pH 8.1,100 mM potassium acetate, 30 mM magnesium acetate) and then used to prepare 0.3 ml of master hybridization mix (100 mM MES, 1M [NaCl], 20mm EDTA, 0.01% Tween 20, 0.1 mg/ml herring sperm DNA (Promega, Madison, Wish.), 0.5 mg/ml acetylated BSA (Invitrogen Carlsbad, Calif.). A mixture of control cRNAs for bacterial and phage genes available from the manufacturer was included in the mix (BioB, BioC, BioD, and cre, at 1.5, 5, 25 and 100 pM, respectively) to serve as tools for comparing hybridization efficiency between arrays and for relative quantitation of measured transcript levels. Before hybridization, the cRNA samples were heated at 94° C. for 5 minutes, equilibrated at 45° C. for 5 minutes and clarified by centrifugation (14,000×g) at room temperature for 5 min. Aliquots of each sample (10 µg of cRNA in 200 µl of the master mix) were hybridized to U133A arrays (Affymetrix) at 45° C. for 16 h in a rotisserie oven set at 60 rpm. The arrays were then washed with non-stringent (6×SSPE, 0.01% Tween-20, 0.005% antifoam) and stringent (100 mM MES, 0.1M NaCl, 0.01% Tween 20), stained with R-Phycoerythrin Streptavidin-(Molecular Probes, Eugene, Oreg.), washed again and scanned by an argon-ion laser scanner with the 560-nm long-pass filter (Molecular Dynamics; Affymetrix). Data analysis was performed by using MAS5.0 software (Affymetrix, Santa Clara, Calif.). The software includes algorithms that determine whether a gene is absent or present (absolute call) and whether the expression level of a gene in an experimental sample is significantly increased or decreased (difference call) relative to a control sample. To assess differences in gene expression, Affymetrix used the "Signal Log Ratio Algorithm" which calculates signal log ratio values using a one-step Tukey's Biweight method by taking a mean of the log ratios of probe pair intensities across the two arrays. Fold change values were calculated using the following formula: $2^{Signal\ Log\ Ratio}$, if Signal Log Ratio$\geq 0$; $(-1)*2^{-(Signal\ Log\ Ratio)}$, if Signal Log Ratio<0 (Affymetrix GeneChip Expression Analysis manual).

EXAMPLE 5

Inhibition of IKKα Gene Expression by siRNA Directed to IKKα in HeLa Cells.

FIG. 1 demonstrates that siRNA of IKKα inhibits mRNA expression of IKKα in HeLa cells. HeLa cells were transfected with IKKα_3 (SEQ. ID. NO. 2) or IKKα_3vt inverted control of oligos of IKK_3 (SEQ. ID. No. 3). by OLIGOFECTAMINE™ using the methods described herein. IKKα mRNA copy numbers were determined by TaqMan™. A 3 fold reduction was found in samples receiving the siRNA relative to samples that had received the control.

EXAMPLE 6

IKKα SiRNA does not Inhibit IKKβ Expression.

IKKα_3 siRNA specifically inhibited the mRNA expression of IKKα but had no effect on IKKβ mRNA expression as shown in FIG. 1 and Table I. This is expected since the sequence of IKKα siRNA was designed to specifically target IKKα mRNA but not the IKKβ mRNA. Thus, IKKα_3 siRNA is demonstrated to be a specific IKKα inhibitor with no crossing activity towards IKKβ.

EXAMPLE 7

Inhibition of IKKα Expression Modulated the Expression of other Genes in the NF-κB Pathway.

Table 1 shows selected IKKα-regulated genes listed in order of their mRNA fold changes in 2 hr TNFα stimulated HeLa cells treated with IKKα siRNA (IKKα_3) vs. 2 hr TNFα stimulated HeLa cells treated with inverted control siRNA. Data were obtained by DNA microarray studies using Affymetrix U133A chips. Results from two independent chip hybridizations are shown. The mRNA of IKKβ and house keeping genes such as beta Actin and GAPDH were not affected by IKKα siRNA (NC, no change call by Affymetrix MAS 5.0 analysis). Inhibition of IKKα expression by IKKα-3 siRNA decreased the expression of known NF-κB-dependent genes such as IL-6, IL-8, IL-11, Cox-2, Dihydrodiol dehydrogenase 1, TNF-induced proteinIntegrin, Urokinase-type plasminogen activator receptor; Intercellular adhesion molecule 1 (CD54), Bone morphogenetic protein 2, Interferon-stimulated protein, 15 kDa, Superoxide dismutase 2 and GRO1. These genes are understood to be NF-κB targets. Pahl H L, *Oncogene* (1999)18, 6853–6866; Li X et al, 2002, *J. Biol. Chem*, 277: 45129–45140.

TABLE 1

| Accession | Gene name | F Id changes (IKKα siRNA + TNF_vs_ctrl siRNA + TNF) Exp. 1 | Exp. 2 | TNF stimulation |
|---|---|---|---|---|
| M13436 | Inhibin, beta A | −10.6 | −7.4 | Yes |
| NM_002133 | Heme oxygenase (decycling) 1 | −5.5 | −5.9 | No |
| AF043337 | Interleukin 8 | −2.5 | −2.3 | Yes |
| NM_001353 | Dihydrodiol dehydrogenase 1 | −2.3 | −1.9 | NO |
| NM_014350 | TNF-induced protein | −2.2 | −1.8 | Yes |
| NM_002205 | Integrin, alpha 5 | −2.0 | −2.3 | No |
| AY029180 | Urokinase-type plasminogen activator receptor | −1.9 | −1.8 | No |
| NM_000201 | Intercellular adhesion molecule 1 (ICAM1/CD54) | −1.7 | −2.0 | Yes |
| M24915 | CD44 antigen | −1.6 | −1.7 | Yes |
| AA583044 | Bone morphogenetic protein 2 | −1.6 | −1.4 | yes |
| NM_000600 | Interleukin 6 | −1.5 | −1.5 | Yes |
| NM_000963 | Cox2 | −1.5 | −1.7 | Yes |
| NM_000641 | Interleukin 11 | −1.5 | −1.6 | Yes |
| NM_005101 | Interferon-stimulated protein, 15 kDa | −1.5 | −1.6 | Yes |
| W46388 | Superoxide dismutase 2 | −1.4 | −1.8 | Yes |
| NM_001511 | GRO1 oncogene | −1.4 | −1.5 | yes |
| M33197 | GAPDH | NC | NC | No |
| X00351 | Actin, beta | NC | NC | No |
| AF080157 | IKKα | −3.1 | −2.8 | No |
| AF080158 | IKKβ | NC | NC | No |

NF-κB activity is modulated by inhibition of IKKα as shown in NF-κB reporter assay system.

EXAMPLE 8

Figure 3:
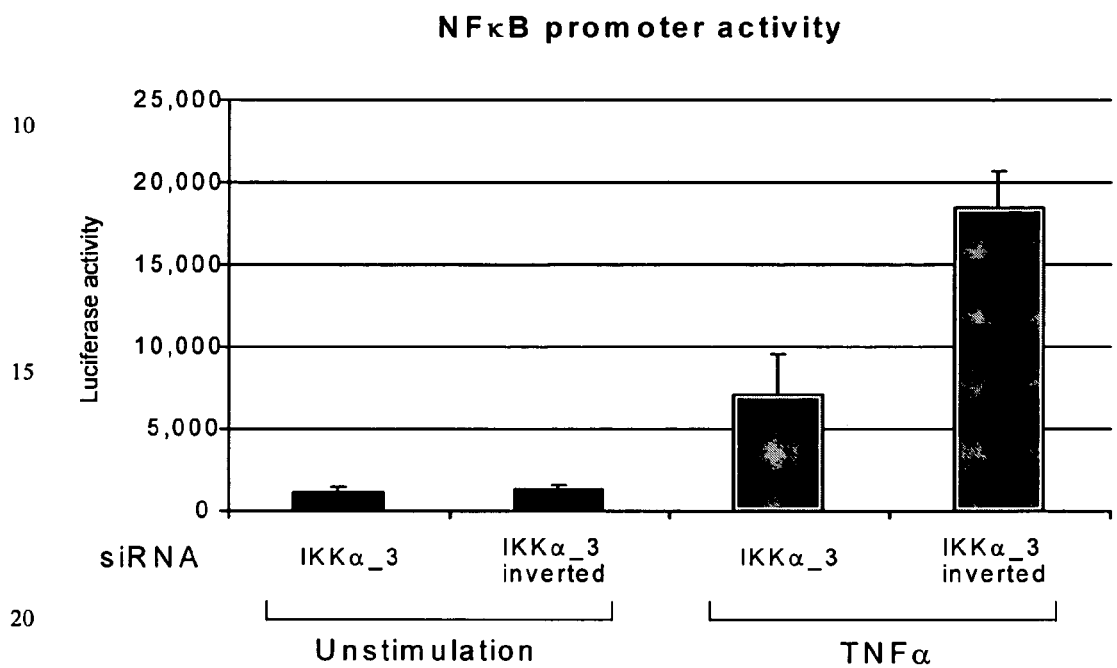
FIG. 3 shows IKKα siRNA inhibits NF-κB activity in HeLa cells transfected with luciferase reporter gene.

The inhibition of IKKα expression modulated the activity of NF-κB in NF-κB-dependent reporter assay. FIG. 3 shows that TNFα-induced NF-κB-dependent luciferase activity was inhibited by siRNA of IKKα. The pNF-κB-Luc plasmid contains NF-κB promoter elements which can be activated by NF-κB. Downstream of the promoter is the luciferase reporter gene. When activation of NF-κB is induced by TNFa, NF-κB will activate the artificial promoter and the promoter will drive the luciferase reporter gene expression. In this experiment, we used HeLa cells that had been stably transfected with the pNF-κB-Luc reporter (Stratagene: 219078, La Jolla, Calif.).

Cells were transfected with siRNA as follows:

6 μg of siRNA duplex and 100 μl of Opti-MEM were mixed. In a separate tube 6 μl Oligofectamine and 24 μl Opti-MEM were incubated for 10 minutes at room temperature. The samples were then mixed and incubated for 25 minutes at room temperature before 64 μl of fresh Opti-MEM was added to obtain a final solution of 200 μl. Finally, 200 μl of siRNA-transfection reagent was added to cultured cells seeded 24 hours prior to the transfection in antibiotics-free medium. Two days later cells were stimulated with TNFα (10 ng/ml) for 24 hours. Cells were then harvested and counted. $5 \times 10^5$ cells in 100 μl of PBS were added to wells of 96-well plate and the luciferase activity was measured by LucLite Luciferase Reporter Gene Assay Kit (Packard BioScience, The Netherlands). The luciferase activity was induced by TNFα (comparing IKKα_3inverted+TNF vs. IKKα_3inverted_unstim, FIG. 3) due to activation of NF-κB. However, such induction was significantly reduced (~3 fold reduction) by IKKα_3 siRNA (comparing IKKα_3+TNF vs. IKKα_3_unstim, FIG. 3). Thus IKKα_3 siRNA blocked TNFα-induced NF-κB activity in gene transcription. The data demonstrate that IKKα plays an important role in TNFα-induced NF-κB-mediated gene transcription.

EXAMPLE 9 siRNA of IKKα inhibits IL-6 and IL-8 expression in HeLa cells

Figure 2:
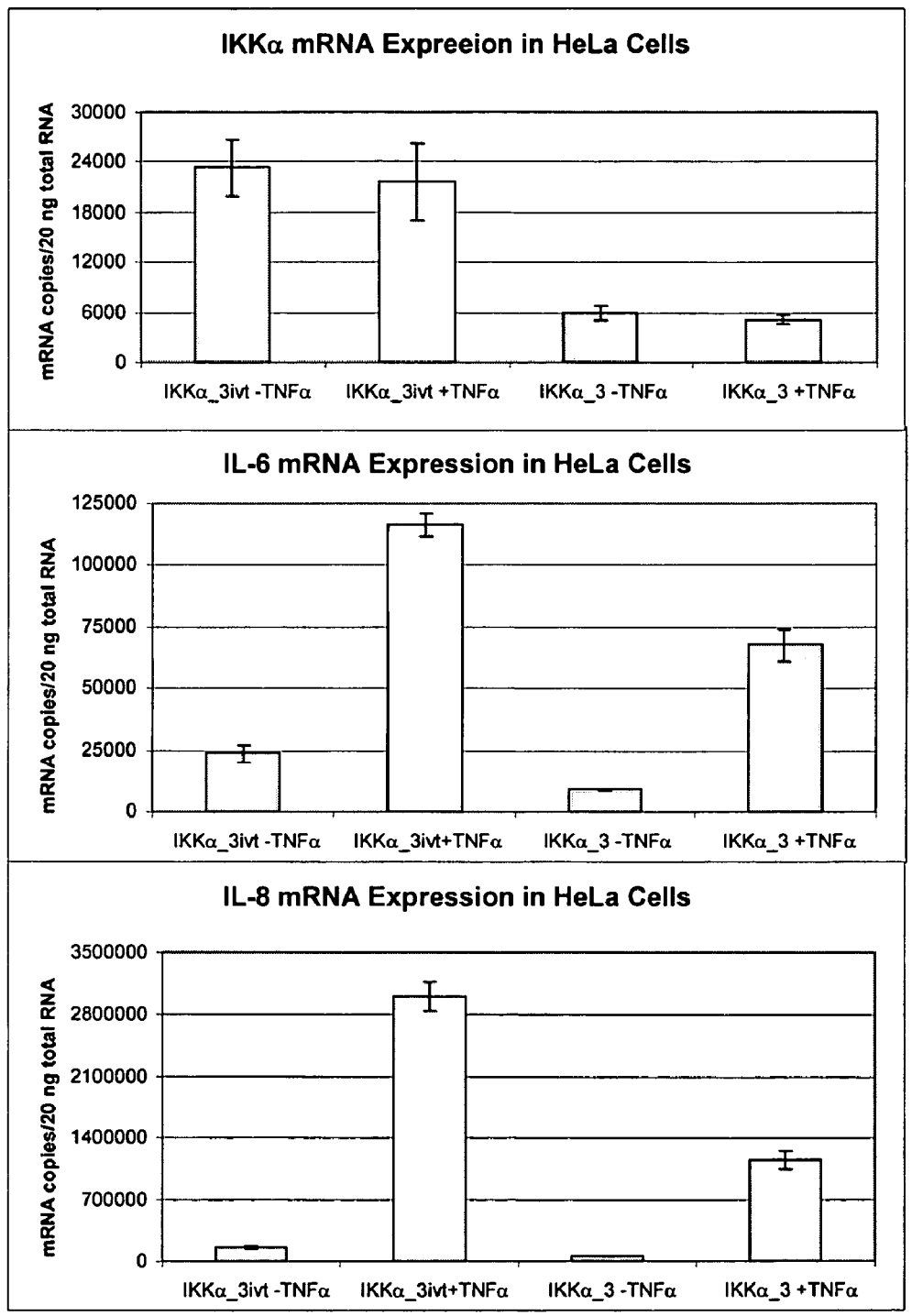
FIG. 2 shows siRNA directed to IKKα inhibits IKKα, IL-6 and IL-8 expression in HeLa cells.

FIG. 2 show that siRNA of IKKα inhibits the expression of proinflammatory genes under the influence of the genes in the NF-κB pathway including IL-6 and IL-8 in HeLa cells. HeLa cells were transfected according to the methods described herein. An approximately 2 fold reduction in the expression of IL-6 was found in TNFα stimulated cells. In un-stimulated cells there was approximately 2 fold reduction in IL-6 mRNA. A 2.6 fold reduction in the level of IL-8 mRNA in TNFα stimulated HeLa cells was found and approximately 2.6 fold reduction was found IL-8 mRNA in unstimulated HeLa cells. These data show the correlation between the level of IKKα activity and the level of expression of genes that are under the influence of the NF-κB pathway.

The level of IL-6 and IL-8 have been shown to be elevated in autoimmune and inflammatory disease conditions Ishihara K et al. *Cytokine Growth Factor Rev* (2002), 13:357–68; Mukaida N, *Int J Hematol* (2000),72:391–8. Monoclonal antibody of IL-6 has been used for treatment for systemic lupus erythematosus. A fully human anti-1L8 monoclonal antibody (ABX-1L8) has also been applied to patients with chronic bronchitis and COPD. Therefore, the treatment of inflammatory disease by inhibitors IL-6-IL-8 activity is demonstrated as a method for testing representative autoimmune and inflammatory diseases.

In addition to IL-6 and IL-8 which are important targets for inflammatory diseases and autoimmune diseases (see above), many other IKKα-regulated genes (Table I) are also mediators of inflammatory diseases and autoimmune diseases.

Cyclooxygenase 2 (Cox2), also known as prostaglandin endoperoxide synthase 2, is the key enzyme required for the conversion of arachidonic acid to prostaglandins which regulate immunity and inflammation (Harris S G et al (2002) *Trends in Immunology* 23:144–50; Turini M E and DuBois R N. (2002) *Annual Review of Medicine* 53:35–57). Cox2 mediates inflammation and selective Cox2 inhibitors have been shown to be potent antiinflammatory agents (Rodrigues C R. et al, 2002, Current Medicinal Chemistry. 9:849–67).

Inhibin, beta A (Activin A) is a member of the transforming growth factor beta (TGF-beta) superfamily and functions in inflammatory pathways. Jones K L. et al (2000) *Endocrinology* 141:1905–8; Yu, J. et al (1997) *Cytokines Cellular & Molecular Therapy* 3:169–77. There is correlation between inhibin secretion and damage of seminiferous tubules in a model of experimental autoimmune orchitis (Suescun Mo. et al, 2001, Journal of Endocrinology 170: 113–20).

Adhesion molecules such as/intercellular adhesion molecule-1 (ICAM1), integrin alpha 5, CD44 and Gro1 are important players in autoimmunity and inflammatory responses. Long-term reversal of established autoimmunity was observed upon the transient blockade of the LFA-ICAM pathway. Bertry-Coussot, L. et al (2002) *Journal of Immu-* nology 168:3641–8. Blockade of the ICAM1 and LFA-1 interaction is an effective approach for immunosuppression. Yusuf-Makagiansar H. et al (2002) *Medicinal Research Reviews* 22:146–67. Integrin alpha 5 is one component of the alpha 5 beta 1 integrin which mediates integrin-independent neutrophil recruitment to endotoxin-induced lung inflammation. Burns J A. et al (2001) *Journal of immunology* 166:4644–4649. Alpha 5 beta 1 integrin activates an NF-κB-dependent program of gene expression important for angiogenesis and inflammation. Klein S et al (2002) *Molecular & Cellular Biology* 22:5912–22. CD44, a cell-adhesion molecule that is ubiquitously expressed on leukocytes and parenchymal cells, functions in several inflammatory diseases. Pure E. et al (2001) *Trends in Molecular Medicine* 7:213–21. Functional activation of lymphocyte CD44 in peripheral blood is a marker of autoimmune disease activity. Estess P. et al (1998) *Journal of Clinical Investigation* 102:1173–82. Antibodies to CD44 prevent central nervous system inflammation and experimental encephalomyelitis by blocking secondary leukocyte recruitment. Brocke S. et al (1999) *Proceedings of the National Academy of Sciences of the United States of America* 96:6896–901.

The invention claimed is:

1. An siRNA composition comprising SEQ. ID NO. 3.
2. An siRNA composition comprising SEQ ID NO: 3 wherein said siRNA is synthetically made.
3. An siRNA composition consisting of SEQ. ID. NO. 3 and its full complement.

* * * * *